United States Patent [19]
Repice et al.

[11] Patent Number: 5,702,355
[45] Date of Patent: Dec. 30, 1997

[54] PORTABLE ADJUSTABLE TRACTION APPLIANCE TO TREAT CARPAL TUNNEL SYNDROME AND OTHER PROBLEMS OF THE WRIST

[75] Inventors: Ronald M. Repice, 640 Georgetown Rd.; Ronald M. Repice, II, 299 Stanton Ct., both of Glen Mills, Pa. 19342; Harold E. Clupper, West Chester, Pa.

[73] Assignees: Ronald M. Repice; Ronald M. Repice, II, both of Glen Mills, Pa.

[21] Appl. No.: 783,632

[22] Filed: Jan. 14, 1997

[51] Int. Cl.⁶ .................................................. A61F 5/04
[52] U.S. Cl. .......................... 602/21; 602/5; 602/12
[58] Field of Search .................... 602/5, 6, 12, 15, 602/16, 21, 25, 36, 39, 61, 62, 63, 64

[56] References Cited

U.S. PATENT DOCUMENTS

| | | | |
|---|---|---|---|
| 1,233,112 | 7/1917 | Nylander | 602/12 |
| 4,485,808 | 12/1984 | Hepburn | 602/5 |
| 4,522,197 | 6/1985 | Hasegawa | 128/26 |
| 4,619,250 | 10/1986 | Hasegawa | 128/26 |
| 4,671,258 | 6/1987 | Barthlome | 128/26 |
| 4,899,763 | 2/1990 | Sebastian et al. | 128/878 |
| 5,014,689 | 5/1991 | Meunchen et al. | 128/77 |
| 5,092,318 | 3/1992 | More et al. | 602/27 |
| 5,254,078 | 10/1993 | Carter et al. | 602/21 |
| 5,279,545 | 1/1994 | Reese | 602/21 |
| 5,376,066 | 12/1994 | Phillips et al. | 602/21 |
| 5,441,058 | 8/1995 | Fareed | 128/898 |
| 5,468,220 | 11/1995 | Sucher | 602/21 |
| 5,611,735 | 3/1997 | Jackson | 602/21 |

*Primary Examiner*—Stephen R. Crow
*Attorney, Agent, or Firm*—Caesar, Rivise, Bernstein, Cohen & Pokotilow, Ltd.

[57] ABSTRACT

A portable appliance for treating carpal tunnel syndrome and/or other problems of the wrist of a person. The appliance comprises a releasably securable sleeve means for securement to a person's forearm, a stationary member positioned on the sleeve means, a moveable member slidably coupled to the stationary member, a cuff means secured to an end of the moveable member and a bias means coupled between the stationary member and the moveable member. The bias means is provided for urging the moveable member to slide from a retracted position to an extended position thus causing the cuff means to securely engage a portion of the person's hand adjacent the person's wrist to apply a predetermined tensile load to the person's wrist in a direction parallel to the longitudinal axis of the forearm.

28 Claims, 9 Drawing Sheets

PORTABLE ADJUSTABLE TRACTION APPLIANCE TO TREAT CARPAL TUNNEL SYNDROME AND OTHER PROBLEMS OF THE WRIST

BACKGROUND OF THE INVENTION

This invention relates generally to medical equipment and more particularly to a portable adjustable traction appliance for treating carpal tunnel syndrome and other disorders of the wrist, e.g., a strain, sprain or subluxation, by applying tension thereto.

Carpal tunnel syndrome is the result of a compromised or narrowed carpal canal leading to compression injury of the median nerve in the wrist. The carpal tunnel is the canal in the wrist through which the median nerve and flexor tendons pass from the forearm to the hand. Prolonged repetitive motion at a keyboard is a common, but by no means the only cause of carpal tunnel syndrome.

Various traction machines are commercially available for applying traction to selected portions of the anatomy of a person to treat some medical condition or problem of the person. For example, Barrington Equipment Company, of Wauconda, Ill. presently markets a pneumatic traction machine, believed to be manufactured by Para Tech Industries, Inc. under the trade designation Para Tech CTD-MARK I for applying traction to the wrist of a person suffering from carpal tunnel syndrome. While this device appears suitable for its intended purposes, it leaves much to be desired from the standpoint of ease of use and patient comfort.

In particular, the machine is of a fixed height so the forearm of the person being treated has to be oriented horizontally. To achieve that end the person must seat himself/herself so that his/her forearm is at the predetermined appropriate height for the application of traction thereto. Depending upon the height of the person, he/she may have to sit bent or hunched over (if the machine is too low for him/her), or else sit unnaturally erect and upright (if the machine is too high for him/her) to be in the proper position for the application of traction to his/her forearm and wrist. This can result in patient discomfort or tiring, particularly for treatments requiring long duration traction.

In our copending U.S. application Ser. No. 08/554,117 filed on Nov. 6, 1995, there is disclosed a device for use on a traction machine which overcomes many of the drawbacks of the prior art systems. In particular, the device disclosed in that application is arranged to be readily attached to a conventional traction machine. Once attached, the device provides height adjustability to the traction machine so that traction may be properly applied to the wrist of a person, irrespective of the height of the person.

While the traction device disclosed in our aforementioned application overcomes many of the disadvantages of the prior art, it still leaves something to be desired from several standpoints. For example, while it is compact and portable, it must be attached to a traction machine, which is not easily transportable.

There are also several appliances in the prior art for treating carpal tunnel syndrome and other wrist disorders which also appear to be portable. Significantly, however, these prior art appliances operate by means other than the application of tension to the wrist. As will be recognized by those skilled in the art the application of tension to the wrist is a particularly effective treatment modality. One such prior art appliance is disclosed in U.S. Pat. No. 5,468,220 (Sucher). That appliance is a bracelet-like device designed to be worn over the user's wrist. Pads are provided on the bracelet for applying small amounts of pressure to locations on the user's wrist and palm to ostensibly flatten the palm and lengthen the carpal ligament, thus supposedly relieving the wearer of symptoms associated with this condition.

Another example of a portable device for treating carpal tunnel syndrome is disclosed in U.S. Pat. No. 5,441,058 (Fareed). This patent discloses an adjustable strap or band adapted to be worn around the forearm. The strap is provided with a plurality of inwardly protruding structures thereon that direct pressure to particular muscles in the forearm, without substantially compressing other non-target areas, to provide relief from the condition.

While these devices may be generally suitable for their intended purposes, since they operate to treat carpal tunnel syndrome by the application of pressure and not by the application of tension to the wrist they may not be as effective as desired.

OBJECTS OF THE INVENTION

Accordingly, it is a general object of this invention to provide a traction appliance which overcomes the disadvantages of the prior art.

It is a further object of this invention to provide a traction appliance which can be readily attached to the forearm of a person in order to apply tension to the person's wrist.

It is a further object of this invention to provide a traction appliance that furnishes a level of tension that is adjustable.

It is a further object of this invention to provide a traction appliance which is readily adjustable to enable it to apply traction to the wrist of a person, irrespective of the length of the person's forearm.

It is a further object of this invention to provide a traction appliance that is portable and is arranged for use independent of any other device.

It is a further object of this invention to provide a traction appliance that is comfortable for the wearer.

It is a further object of this invention to provide a traction appliance that is simple in construction.

It is a further object of this invention to provide a traction appliance that is easy for the user to apply and remove from his or her forearm.

SUMMARY OF THE INVENTION

These and other objects of this invention are achieved by providing a portable and adjustable traction appliance for treating carpal tunnel syndrome and other problems of the wrist. The appliance comprises a releasably securable sleeve that is secured to the wearer's forearm, a stationary member positioned on the sleeve, a moveable member slidably coupled to the stationary member, a cuff secured to an end of the moveable member and a bias means coupled between the stationary member and the moveable member. The bias means is provided for urging the moveable member to slide from a retracted position to an extended position thus causing the cuff to securely engage a portion of the person's hand adjacent the person's wrist to apply a predetermined tensile load to the person's wrist in a direction parallel to the longitudinal axis of the forearm.

DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF THE PREFERRED EMBODIMENTS

Figure 1:
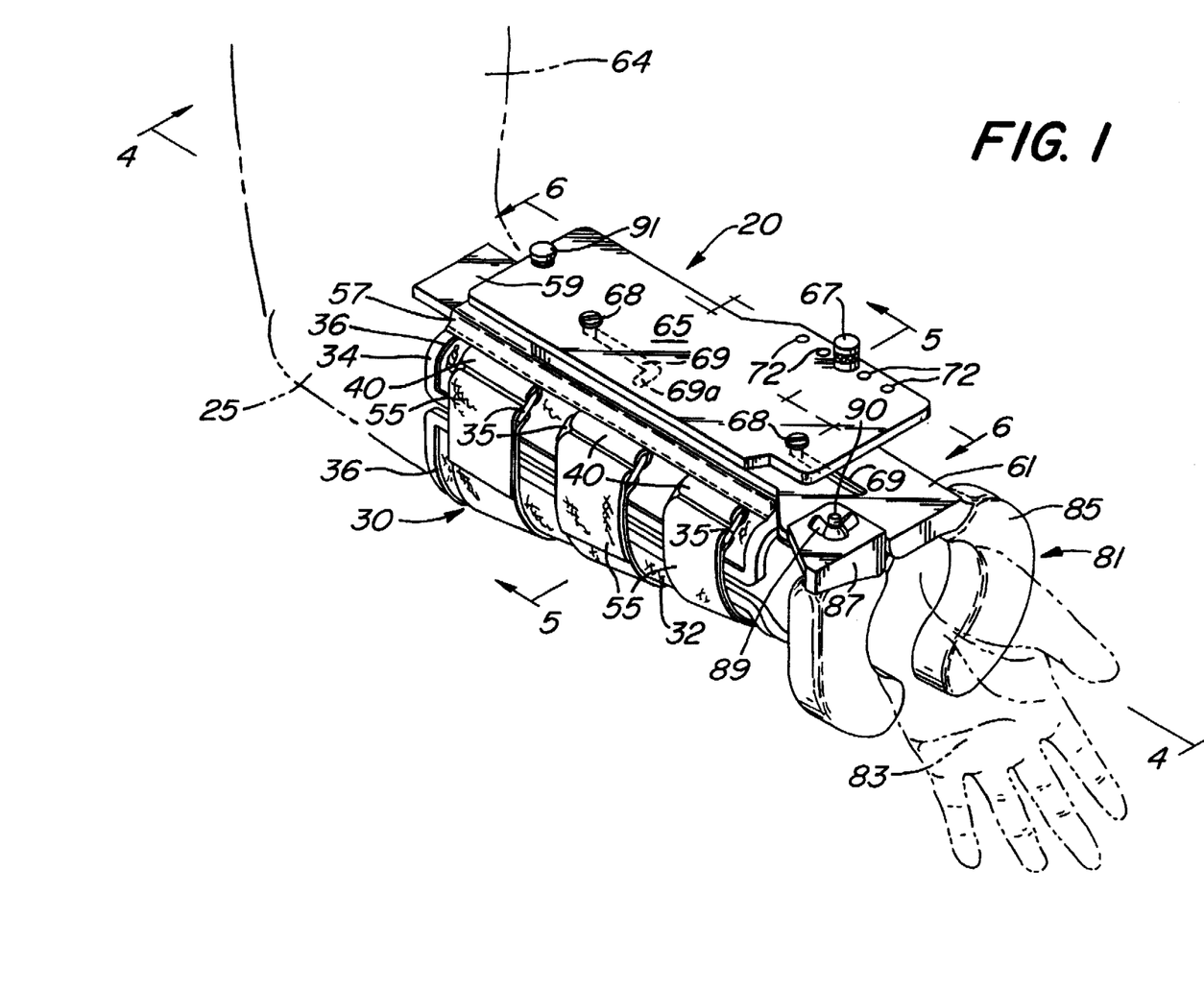
FIG. 1 is an isometric view of the preferred embodiment of the present invention.
Figure 5:
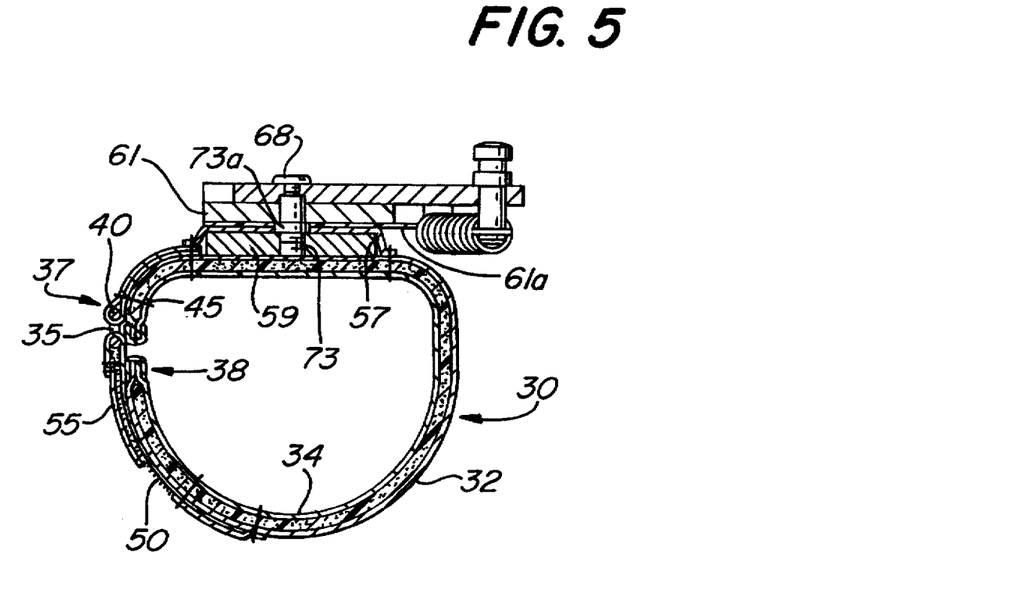
FIG. 5 is an enlarged sectional view taken along line 5—5 of FIG. 1.
Figure 6:
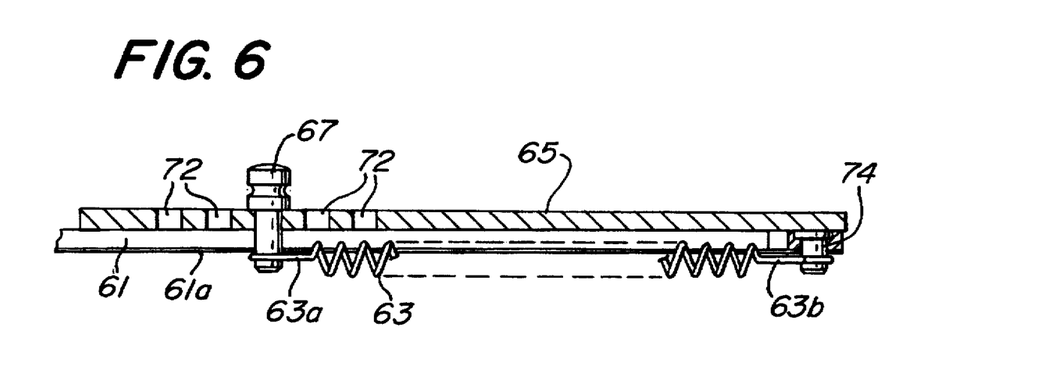
FIG. 6 is an enlarged sectional view taken along line 6—6 of FIG. 1.

Referring now to various figures of the drawing where like reference numerals refer to like parts, in FIG. 1 there is shown generally at 20 the preferred embodiment of the portable adjustable traction appliance. The appliance 20 attaches to the forearm 25 of the wearer by means of an adjustable sleeve 30 that is adapted to be circumferentially fitted around the forearm 25. As shown in FIGS. 1 and 5, the adjustable sleeve 30 comprises an outer layer 32 that is formed of any suitable flexible material, e.g., fabric, plastic, or leather. To provide comfort to the wearer, the sleeve 30 is also provided with a padded inner layer 34 (FIG. 5) which extends over the entire inner surface of the sleeve 30 and wraps over the edges of the sleeve and attaches thereto by stitching 36.

Figure 3:
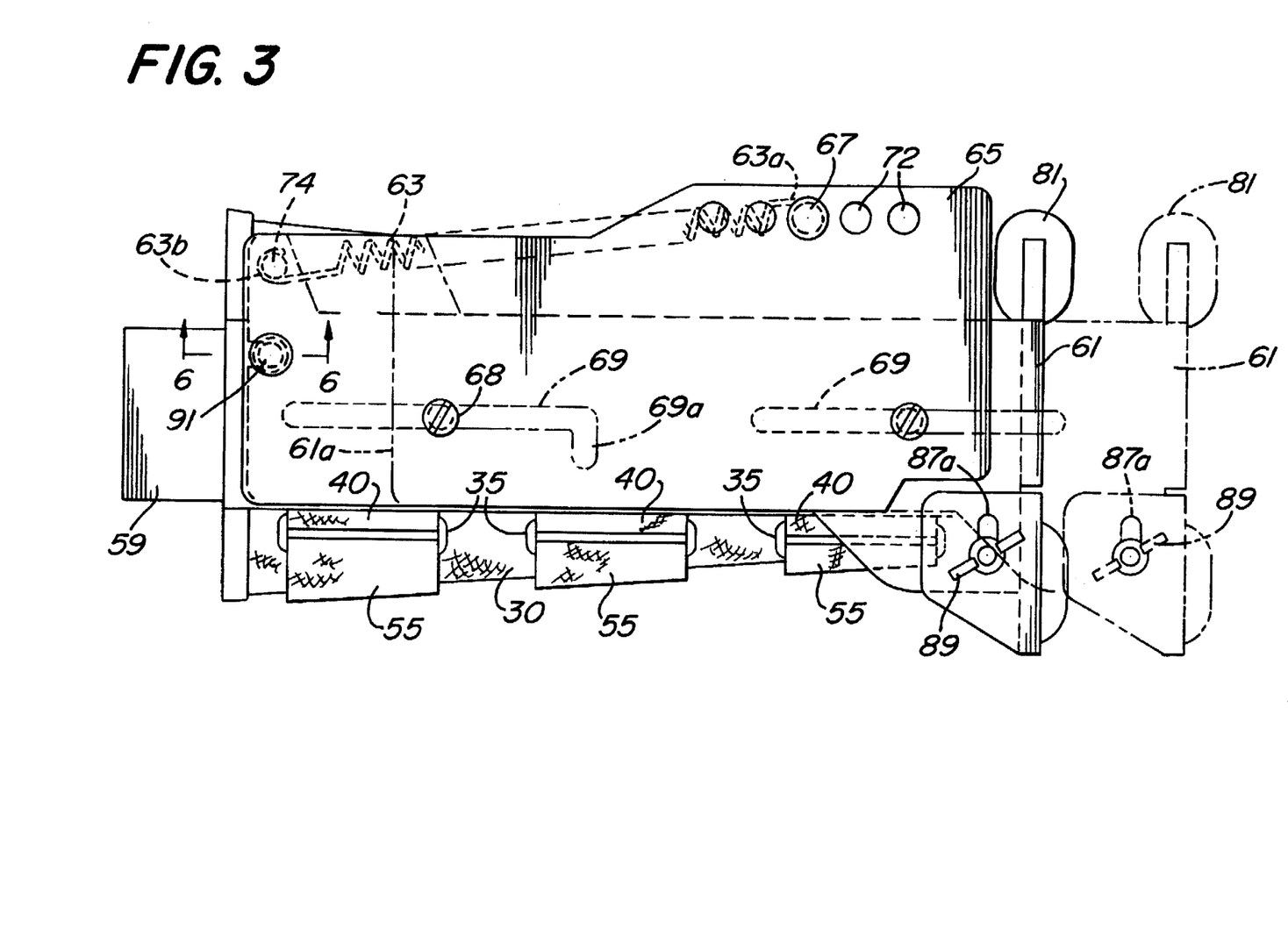
FIG. 3 is a top view of the preferred embodiment of the present invention illustrating the moveable member in the retracted position in solid lines and in the extended position in phantom lines.

Referring now to FIGS. 3 and 5, a plurality, e.g., three, metal D-rings 35 are secured to a first end 37 of sleeve 30 by means of corresponding fabric loops 40 that are secured to the sleeve 30 by stitching 45. Each fabric loop 40 encircles a leg of its corresponding D-ring 35. As best shown in FIG. 5, a VELCRO (R) type looping patch 50 is sewn to a second end 38 of the sleeve 30 by stitching. A plurality of straps 55, e.g., three (FIG. 1), extend from the second end 38 of the sleeve 30. Attached to each strap 55 is a VELCRO (R) type hooking element arranged to engage with the looping patch 50. The straps 55 are arranged to be disposed through the corresponding D-rings 35 and releasably engage with the looping patch 50. In this manner, the sleeve 30 can be held closely, yet comfortably, around the person's forearm 25, irrespective of the size of the person's forearm 25.

Figure 2:
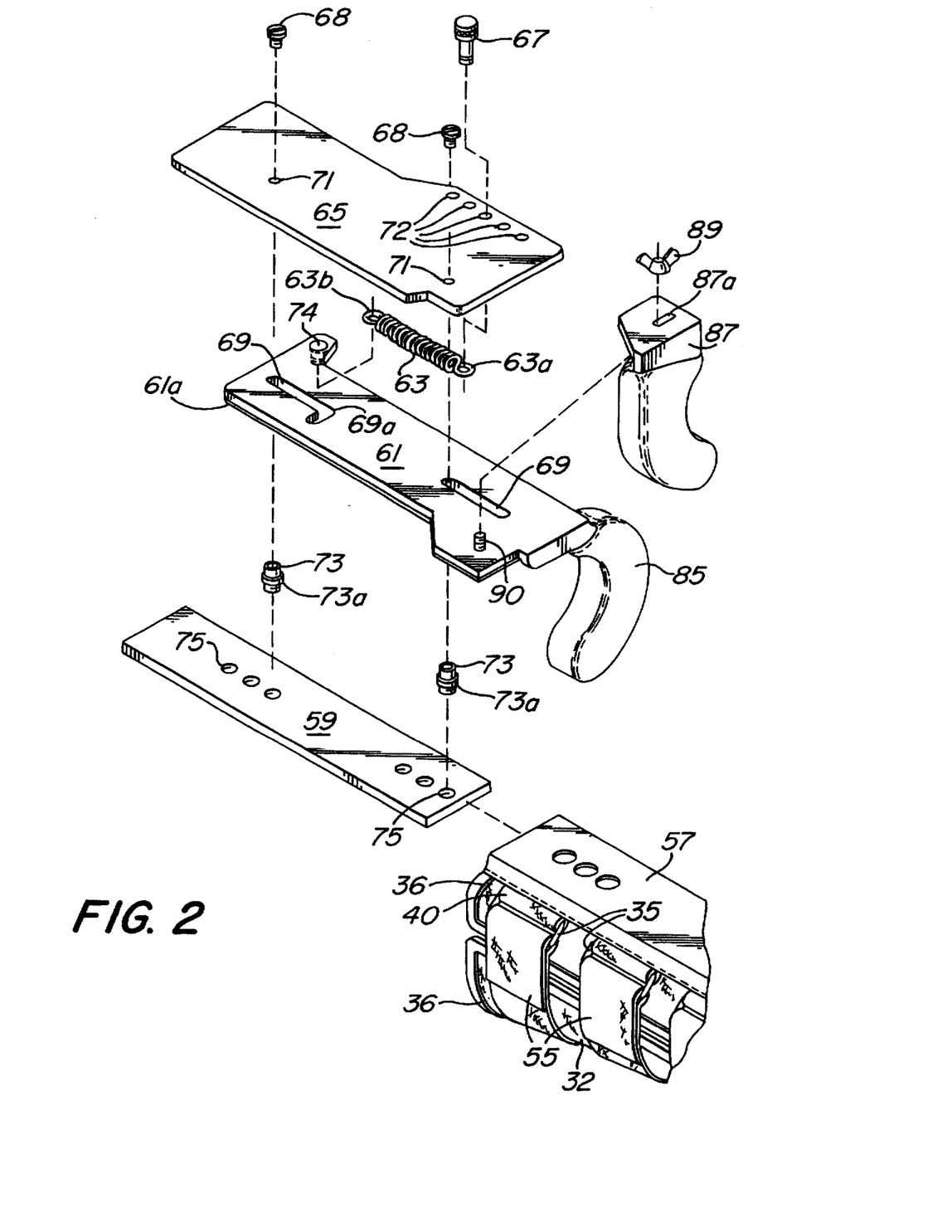
FIG. 2 is an exploded isometric view revealing the various components of the preferred embodiment of the present invention.

As shown in FIGS. 1, 2 and 5, a fabric piece 57 is sewn to the top of sleeve 30 to form an open-ended pocket into which a base plate 59 is inserted.

As shown in FIG. 2, a retainer plate 65 is mounted to the base plate 59 by means of threaded fasteners 68 or other suitable fastening means that extend through openings 71 in the retainer plate 65 and into threaded bosses 73 which mount into threaded openings 75 in the base plate 59. A moveable member 61 is provided with a plurality, e.g., two, elongated slots 69 and 69a and is slidably disposed between the retainer plate 65 and the fabric piece and is mounted to the base plate 59 by means of the fasteners 68 extending through the slots 69 and 69a. Each threaded boss 73 is provided with a shoulder 73a on which the moveable member 61 slides during operation. The base plate 59, moveable member 61 and retainer plate 65 are formed of any suitable material and preferably are formed of a plastic material such as lexan.

Bonded to the bottom surface of the moveable member 61 is a low-friction layer 61a in order to minimize friction between the moveable member 61 and the fabric piece 57 on which it slides during operation. The low-friction layer 61a is formed of any suitable material, e.g., lexan.

As an alternative to the use of a low friction layer 61a, a separate low-friction shim member (not shown) is fastened to and disposed on top of the fabric piece 57. The low-friction shim member (not shown) acts as a layer that prevents contact between the moveable member 61 and the fabric piece 57 during operation, and also acts to minimize friction created during sliding of the moveable member 61. The shim is formed of any suitable material, e.g., lexan, and is the approximate length and width of the fabric piece 57.

Figure 4:
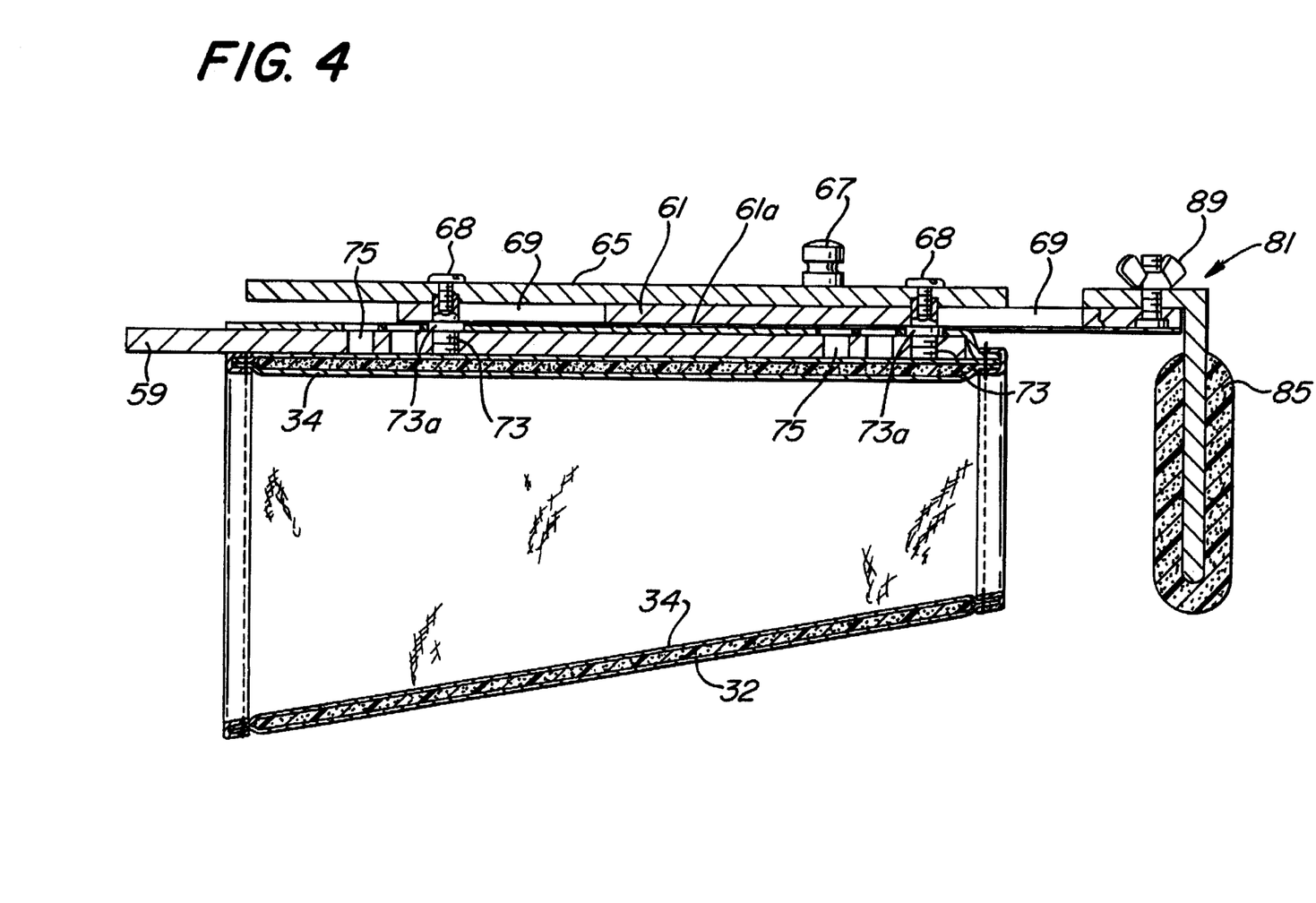
FIG. 4 is an enlarged sectional view taken along line 4—4 of FIG. 1 illustrating the moveable in the extended position.

Referring now to FIGS. 1, 2 and 4, a cuff assembly 81 is secured to the distal end of the moveable member 61. As best shown in FIG. 1, the cuff assembly 81 is oriented generally at right angles to the central axis of the forearm 25 and the wearer's hand 83 is shown as being disposed through the cuff assembly 81. The cuff assembly 81 basically comprises a fixed arcuate member 85 and an adjustable arcuate member 87. The adjustable arcuate member 87 is provided with a slot 87a to enable slidable mounting over a threaded post 90 located on moveable member 61. The adjustable arcuate member 87 is secured to the moveable member 61 by means of a wing nut 89. The fixed and adjustable arcuate members form an opening through which the wearer's wrist is disposed during use. The opening can be enlarged or reduced based upon the size of the wearer's wrist and hand 83 by adjusting the adjustable arcuate member 87. The arcuate members are padded to provide comfort to the wearer during use. In use, the arcuate members 85 and 87 should be positioned closely, yet comfortably around the person's wrist.

Figure 7:
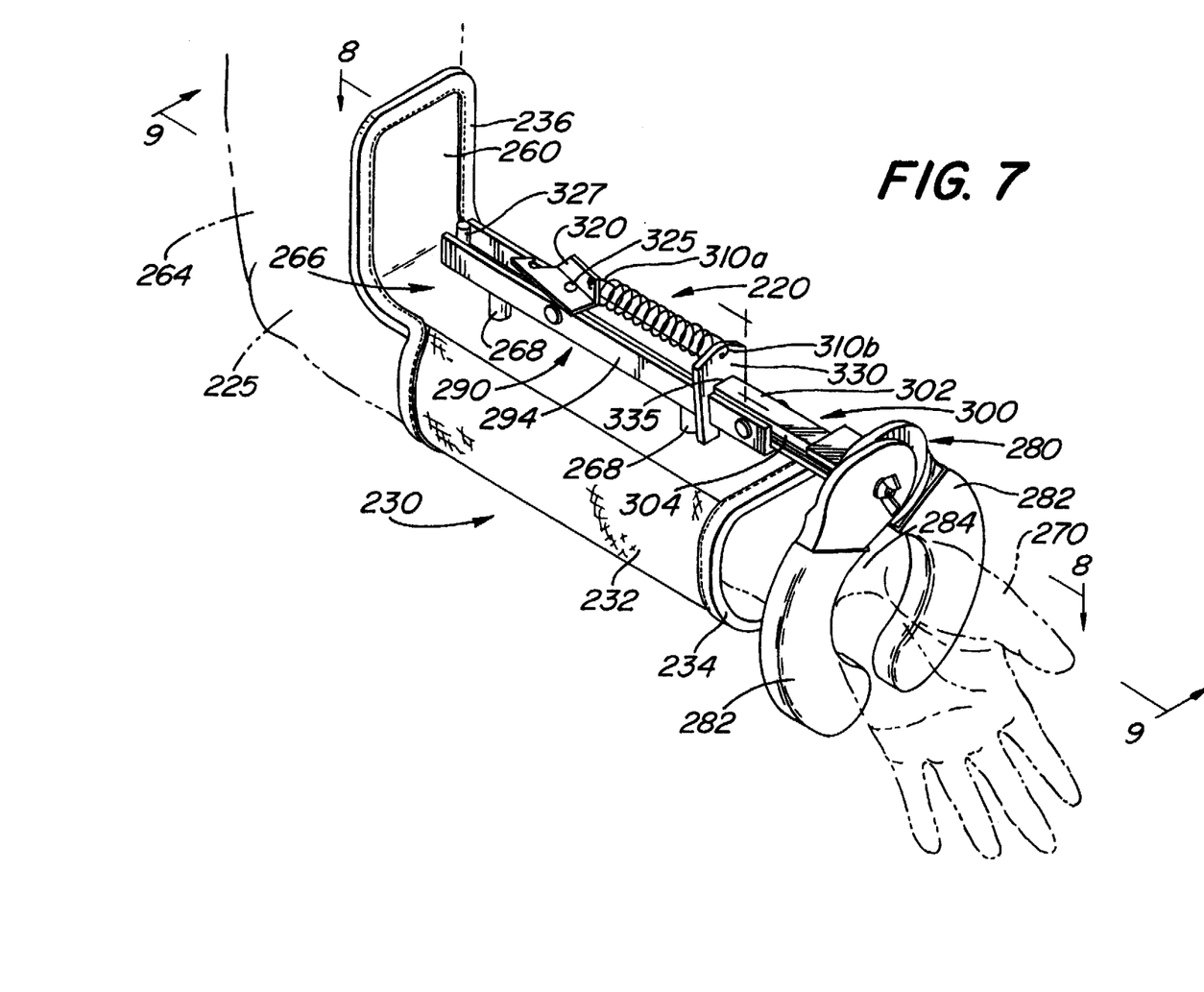
FIG. 7 is an isometric view of a second embodiment of the present invention.

Referring now to FIGS. 2, 3 and 7, there is shown therein a tensioning spring 63 which at one end 63a is mounted to the retainer plate 65 by attachment to a peg 67 that extends through any one of a plurality of openings 72 in the retainer plate 65. The peg 67 may be inserted in any one of a plurality of openings 72 are provided on the retainer plate 65 to enable adjustment of the tension exerted on the wrist by the tensioning spring 63. At its other end 63b, the tensioning spring is mounted to the moveable member 61 by attachment to a post 74 that extends below the moveable member 61. Referring now to FIG. 3, the tensioning spring 63 is provided to urge the moveable member 61 between a retracted position wherein the cuff assembly 81 is located closer to the sleeve 30 (FIG. 3, shown in solid lines) to an extended position (FIG. 3, shown in phantom lines) wherein the cuff subassembly 81 is located further from the sleeve 30.

As best shown in FIG. 2, the moveable member 61 is provided with the elongated slot 69a which has an abrupt angled portion which forms a dogleg. The moveable member 61 is retained in the retracted position by means of the threaded fastener 68 engaging the sidewall of the dogleg portion of the elongated slot 69a. By moving the moveable member 61 in a lateral direction, the user can disengage the threaded fastener 68 from the dogleg portion of elongated slot 69a thus releasing the moveable member 61 from the retained position.

Upon release of the moveable member 61, the tensioning spring 63 contracts which in turn causes the moveable member 61 to slide toward the extended position. As the moveable member 61 moves to the extended position, it causes the cuff subassembly 81 to securely engage a portion of the person's hand adjacent the person's wrist, whereupon a predetermined tensile load is applied to the person's wrist in a direction parallel to the longitudinal axis of the forearm. The moveable member is shown in the extended position in FIGS. 1, 3 (in phantom) and 4.

As should be appreciated from the foregoing the device 20 of this invention provides various features that places sufficient traction on the carpal ligament, while separating the carpal bones to take pressure off the median nerve, thereby reducing the symptoms of carpal tunnel syndrome.

Figure 8:
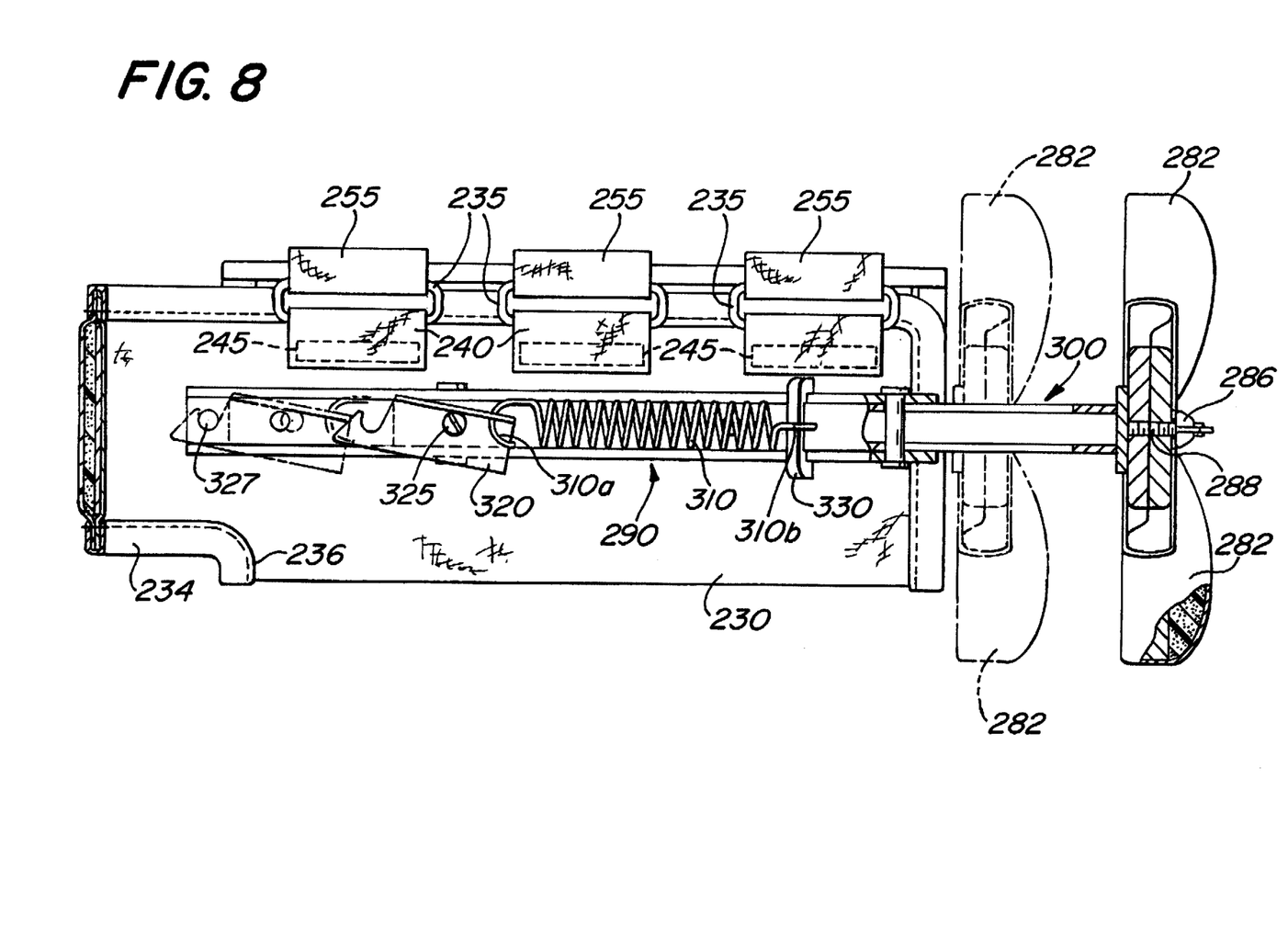
FIG. 8 is an enlarged sectional view taken along line 8—8 of FIG. 7 illustrating the moveable frame in the retracted position in phantom lines and in the extended position in solid lines.
Figure 9:
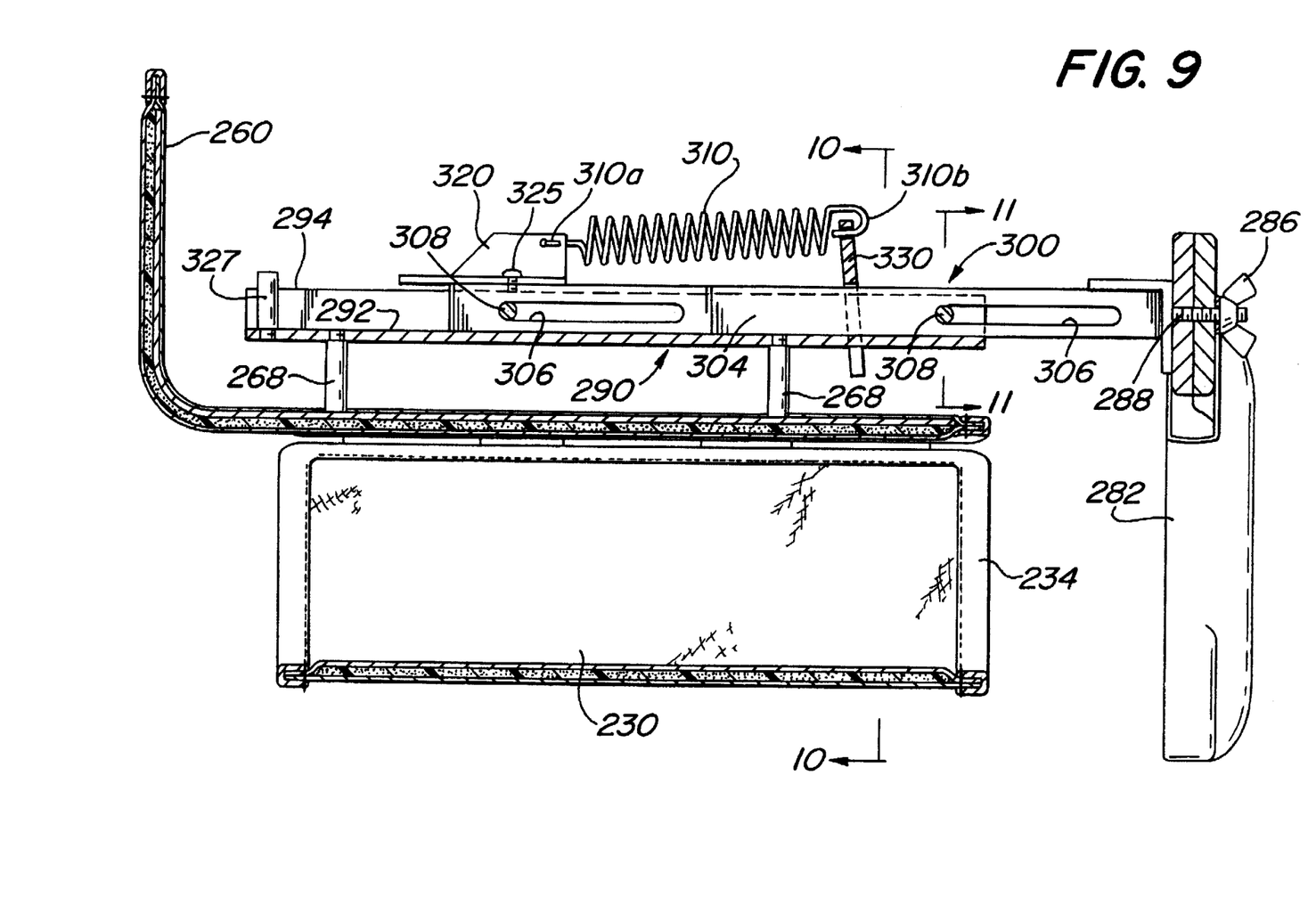
FIG. 9 is an enlarged sectional view taken along line 9—9 of FIG. 7.
Figures 10, 11:
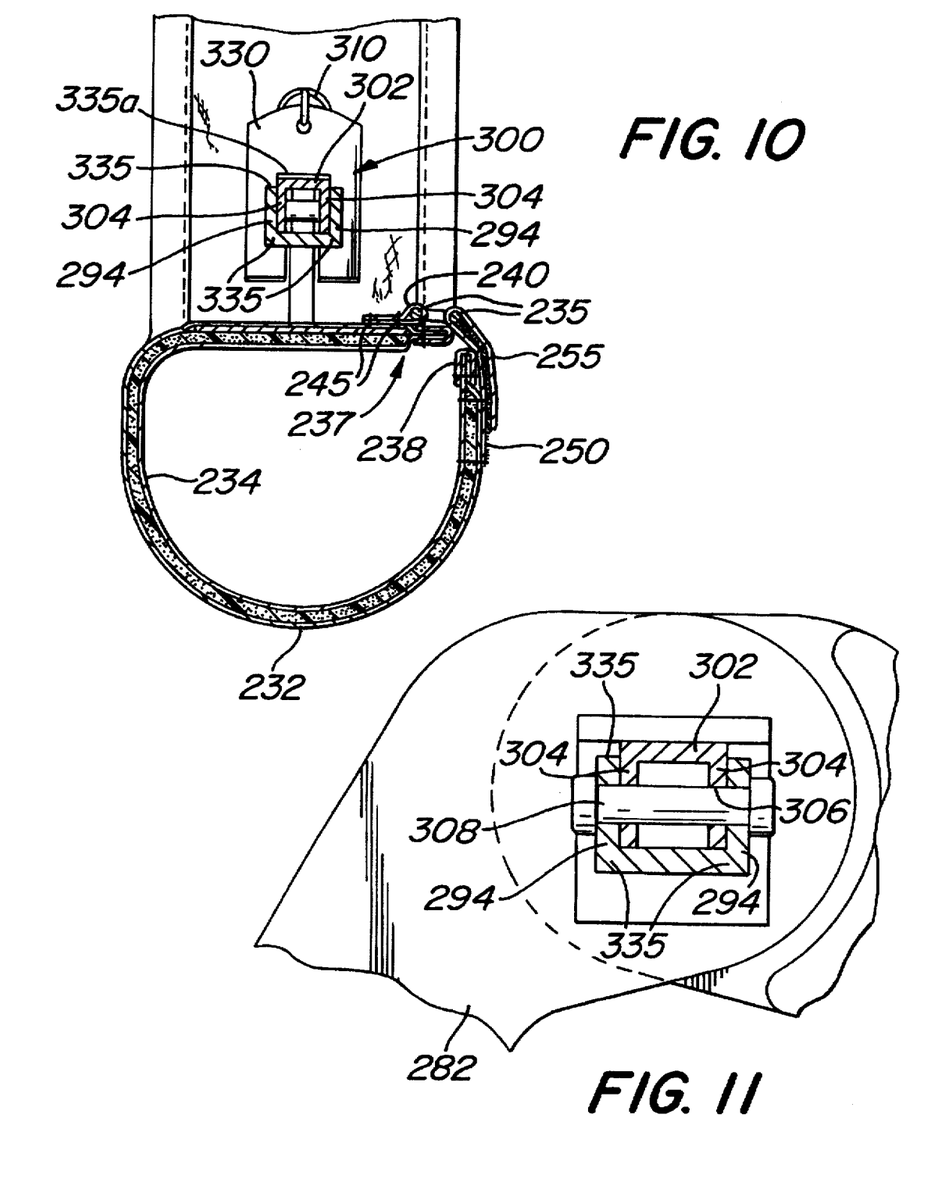
FIG. 10 is an enlarged sectional view taken along line 10—10 of FIG. 9.
FIG. 11 is an enlarged sectional view taken along line 11—11 of FIG. 9.

An alternative embodiment 220 of the portable adjustable traction device of the present invention is shown in FIGS. 7 through 11. The appliance 220 attaches to the forearm 225 of the wearer by means of an adjustable sleeve 230 that is adapted to be circumferentially fitted around the forearm 225. As best shown in FIG. 10, the adjustable sleeve 230 comprises an outer layer 232 that is formed of any suitable flexible material, e.g., fabric, plastic, or leather. To provide comfort to the wearer, the sleeve 230 is also provided with a padded inner layer 234 which extends over the entire inner surface of the sleeve 230 and wraps over the edges of the outer layer 232 and is attached to the outer layer 232 by stitching 236 (FIG. 7).

Referring now to FIGS. 8 and 10, a plurality, e.g., three, metal rings 235 are secured to a first end 237 of sleeve 230. As best shown in FIG. 10, the rings 235 are held to the sleeve 230 by means of corresponding fabric loops 240 that are secured to the sleeve 230 by stitching 245. Each fabric loop 240 encircles a leg of its corresponding ring 235. A VELCRO (R) type looping patch 250 is sewn to a second end 238 of the sleeve 230 by stitching. A plurality of straps 255, e.g., three (FIG. 8), extend from the second end 238 of the sleeve 230. Attached to each strap 255 is a VELCRO (R) type hooking element arranged to engage with the looping patch 250. The straps 255 are arranged to be disposed through the corresponding rings 235 and releasably engage with the looping patch 250. In this manner, the sleeve 230 can be held closely, yet comfortably, around the person's forearm 225, irrespective of the size of the person's forearm 225.

As shown in FIGS. 7 and 9, the sleeve 230 is also provided with a padded curved extension piece 260 to provide protection to the upper arm 264 of the wearer during use. A spring loaded traction assembly 266 (to be described in detail below) is mounted to the sleeve 230 by means of rivets 268 or other suitable means for fastening.

As best shown in FIGS. 7 and 8, the hand 270 of the wearer is shown as being disposed through a cuff assembly 280. The cuff assembly 280 basically comprises a pair of arcuate members 282 that form an opening 284 through which the wearer's wrist is disposed during use. The opening 284 can be enlarged or reduced based upon the size of the wearer's wrist and hand 270. In use, the arcuate members 282 should be positioned closely, yet comfortably around the person's wrist. The arcuate members 282 are attached to the traction subassembly 266 by mounting over a common threaded shaft 288 and are secured thereto by means of a wing nut 286. By loosening the wing nut 286, the arcuate members 282 can be adjusted to create a larger or smaller opening 284 depending upon the size of the wearer's wrist. Each arcuate member 282 is provided with padding to provide comfort to the wearer during operation.

The details of the traction assembly 266 and the operation of the appliance 220 of the instant invention will now be discussed in detail. As shown in FIGS. 7 through 10, the traction assembly 266 comprises a stationary frame 290 that is attached to the sleeve 230 by means of rivets 268 or other suitable means for fastening. The stationary frame 290 is U-shaped and is formed of a bottom wall 292 (FIG. 9) and opposed sidewalls 294 that extend upwardly from bottom wall 292. The sidewalls 294 are provided with through openings (not shown) at opposing locations to enable slidable mounting of a moveable frame 300 within the confines of the stationary frame 290.

Positioned within stationary frame 290 is moveable frame 300. Moveable frame 300 is also U-shaped and comprises a top wall 302 and sidewalls 304 that extend downwardly therefrom. As best shown in FIG. 10, the sidewalls 304 of moveable frame 300 are spaced apart from one another a predetermined distance to fit snugly within side walls 294 of stationary frame 290. As best shown in FIG. 9, each side wall 304 of moveable frame 300 is provided with a plurality of elongated slots 306, e.g., two, that align with the through openings (not shown) in the sidewalls 294 of stationary frame 290. The moveable frame 300 is slidably mounted within the stationary frame 290 by means of bolts 308, extending through the opposed openings in each side wall 294 of stationary frame 290 and through slots 306 in each side wall 304 aligned therewith. Other suitable hardware, e.g., rivets, could be utilized for mounting the moveable frame 300 within the stationary frame 290.

Referring now to FIGS. 7 and 9 there is shown therein a spring 310 which at one end 310a is connected to the moveable frame 300 by attachment to a latch 320 mounted on the frame. The latch 320 is hingedly mounted to the moveable frame 300 by means of a pin 325. Additionally, a post 327 is provided on stationary frame 290. By engaging the latch 320 onto the post 327, the moveable frame is held in substantially overlying relationship with respect to the stationary frame 290 and in this orientation, the traction subassembly 266 is said to be in the retracted position, as best shown by phantom lines in FIG. 8.

Referring now to FIG. 7, the spring 310 is connected at end 310b to the stationary frame 290 by attachment to the upper portion of an adjustable collar 330 disposed around said frame.

As best shown in FIG. 10, the collar 330 has a central opening defined by inner edge 335 that actually surrounds the stationary 290 and moveable 300 frames. As best shown in FIG. 8, when in the retracted position, the spring 310 exerts a tensile force on the collar 330 in the counterclockwise direction. In response, the inner edge 335 of the collar grips the stationary frame 290 thus preventing the collar 330 from sliding proximally along the frames. The inner edge 335 of the collar 330 also provides a gap 335a above the frames to enable free movement of the moveable frame 300 through the collar 330.

By releasing the latch 320 (FIG. 7) from the post 327, the spring 310, which is in tension, contracts and pulls on pin 325 (FIG. 7) which in turn causes the moveable frame 300 to slide and extend distally with respect to the stationary frame 290. The extension of the moveable frame 300 in this direction causes the cuff assembly 280, attached at the distal end of the moveable frame 300, to also move distally and abut the lower portion of the patient's hand 270 so that tension can be provided to the wrist. The tension exerted by the spring 310 may be adjusted to be greater or lesser by simply rotating the collar 330 clockwise by hand and sliding it to a different position along stationary frame 290.

It should be pointed out at this juncture that the subject invention is not limited for use in treating carpal tunnel syndrome. Thus, it can be used to treat other medical problems of the wrist, such as strains, sprains, subluxations, edema, general wrist tenderness and aches, vascular insufficiency and/or neurologia, muscle weakness due to carpal mobility, and to relieve pain due to arthritis, while slowing down its future progression. In addition, the subject invention can be used prophylactically, e.g., as preventive maintenance of the wrist joint.

In addition to the foregoing medical advantages, the subject invention exhibits a number of other advantageous features. In this regard, first, it is a portable self-contained unit and can operate without the need for mounting on a traction machine such as those of the prior art.

Moreover, since the device is fully adjustable, it allows for maximum biomechanical traction without undue patient discomfort. The sleeve is adjustable for maximum stability and bracing.

Without further elaboration, the foregoing will so fully illustrate our invention that others may, by applying current or future knowledge, adopt the same for use under various conditions of service.

What we claim is:

1. A portable appliance for treating carpal tunnel syndrome and/or other problems of the wrist of a person, the person having a forearm and a hand which are joined at the wrist, the forearm having a longitudinal axis, said appliance comprising:

a. releasably securable sleeve means arranged for releasable securement to the forearm of the person;

b. a stationary member fixedly positioned on said sleeve means;

c. a moveable member having an end portion and being slidably coupled to said stationary member for linear movement along a path parallel to the longitudinal axis;

d. cuff means secured to the end portion of said moveable member and being arranged to securely engage a portion of the person's hand adjacent the person's wrist;

e. bias means coupled between said stationary member and said moveable member, said bias means being provided for urging said moveable member to slide from a retracted position wherein said cuff means is located closer to said sleeve means to an extended position, wherein said cuff means is located further from said sleeve means to cause said cuff means to securely engage a portion of the person's hand adjacent the person's wrist, whereupon a predetermined tensile load is applied to the person's wrist in a direction parallel to the longitudinal axis of the forearm; and, f. latching means coupled between said stationary member and said moveable member for retaining said moveable member in said retracted position.

2. The appliance of claim 1 wherein said stationary member comprises a base member fixedly attached to said sleeve means and a retainer member fixedly attached to said base member, said retainer member being in a spaced-apart relationship with said base member and said retainer member substantially overlying said base member, said moveable member being disposed between said base member and said retainer member.

3. The appliance of claim 2 wherein said base member comprises an elongated plate having a plurality of openings and said retainer member comprises an elongated plate having a plurality of openings aligned with the openings in said base member and wherein said moveable member comprises an elongated plate having a plurality of elongated slots oriented parallel to the longitudinal axis, said slots being aligned with said openings in said base and retainer members.

4. The appliance of claim 3 additionally comprising fastening means, said fastening means extending through the openings in said retainer member, through the slots in said moveable member and through the openings in said base member to provide slidable mounting of said moveable member between said retainer member and said base member.

5. The appliance of claim 4 wherein said fastening means comprises a nut and a bolt.

6. The appliance of claim 2 wherein said sleeve means additionally comprises an elongated pocket means mounted thereon and wherein said base means is disposed within said pocket means.

7. The appliance of claim 2 wherein said retainer member additionally comprises a plurality of adjustment holes and wherein said appliance additionally comprises a peg having a shank portion sized for insertion into any one of said holes, said peg being arranged for coupling with said bias means and for insertion into any one of said adjustment holes, said plurality of adjustment holes and peg being provided to establish said predetermined tensile load.

8. The appliance of claim 7 wherein said bias means comprises a coil spring.

9. The appliance of claim 1 wherein said cuff means is arranged to fit snugly around the wrist of the person.

10. The appliance of claim 9 wherein said cuff means is adjustable to accommodate various sized wrists.

11. The appliance of claim 9 wherein said cuff means comprises a first arcuate member and a second arcuate member, said first arcuate member being fixedly secured to the end portion of said moveable member, said second arcuate member being slidably mounted to the end portion of said moveable member to provide adjustably to fit various sized wrists.

12. The appliance of claim 9 wherein the end portion of said moveable member is located at the distal end of said moveable member.

13. The appliance of claim 1 wherein said cuff means is padded.

14. The appliance of claim 1 wherein said sleeve means is adjustable in size to accommodate various sized forearms.

15. The appliance of claim 14 wherein said sleeve means includes cooperating releasably securable hook and loop fastening means.

16. The appliance of claim 1 wherein said sleeve means has an interior surface and is padded.

17. The appliance of claim 1 wherein said stationary member comprises an elongated U-shaped outer frame having a bottom wall and two opposed upward extending sidewalls, and wherein said moveable member comprises an elongated U-shaped inner frame having a top wall and two opposed downward extending sidewalls, said sidewalls of said inner frame being suitably spaced apart from each other to fit within the sidewalls of said outer frame.

18. The appliance of claim 17 additionally comprising fastening means and wherein each sidewall of said inner frame includes an elongated slot extending substantially the length of said stationary member and wherein said sidewalls of said outer frame include a plurality of opposed and spaced apart openings and wherein said inner frame is slidably mounted within said outer frame by said fastening means extending through said opposed openings and through said slots.

19. The appliance of claim 18 wherein said fastening means comprises a rivet.

20. The appliance of claim 18 wherein said fastening means comprises a nut and bolt.

21. The appliance of claim 18 wherein said cuff means is arranged to fit snugly around the wrist of the person.

22. The appliance of claim 18 wherein said cuff means is adjustable to accommodate various sized wrists.

23. The appliance of claim 18 wherein said cuff means comprises two arcuate members that are hingedly connected to each other to fit various sized wrists.

24. The appliance of claim 18 wherein said cuff means is padded.

25. The appliance of claim 18 wherein said sleeve means is adjustable in size to accommodate various sized forearms.

26. The appliance of claim 18 wherein said sleeve means includes cooperating releasably securable hook and loop fastening means.

27. The appliance of claim 18 wherein said sleeve means has an interior surface and is padded.

28. The appliance of claim 18 wherein said bias means comprises a coil spring.

* * * * *